United States Patent [19]

Simms, deceased et al.

[11] 4,351,939

[45] Sep. 28, 1982

[54] SPIRO-QUATERNARY AMMONIUM HALIDES AND N-(2-PYRIMIDINYL)PIPERAZINYLALK-YLAZASPIROALKANEDIONE PROCESS

[75] Inventors: Jack C. Simms, deceased, late of Elberfeld, Ind.; Old National Bank in Evansville, administrator, Evansville, Ind.

[73] Assignee: Mead Johnson & Company, Evansville, Ind.

[21] Appl. No.: 197,416

[22] Filed: Oct. 16, 1980

[51] Int. Cl.$^3$ .............. C07D 401/14; C07D 487/10; C07D 471/10
[52] U.S. Cl. .................. 544/230; 544/231
[58] Field of Search ................ 544/230; 546/16

[56] References Cited

U.S. PATENT DOCUMENTS 3,717,634  2/1973  Wu ........................... 546/16
3,968,216  7/1976  Bouillon et al. ........... 260/326.2

OTHER PUBLICATIONS

Babayan et al., Chem. Abs. 83, 79024f (1975).

Primary Examiner—Mark L. Berch
Attorney, Agent, or Firm—Robert H. Uloth; Robert E. Carnahan

[57] ABSTRACT

Novel spiro-quaternary ammonium halides are disclosed. The new compounds are particularly valuable as intermediates in preparation of N-(2-pyrimidinyl)-piperazinylalkyl derivatives of azaspiroalkanediones such as the psychopharmacologic agent 8-[4-[4-(2-pyrimidinyl)-1-piperazinyl]butyl]-8-azaspiro[4.5]decane-7,9-dione.

4 Claims, No Drawings

SPIRO-QUATERNARY AMMONIUM HALIDES AND N-(2-PYRIMIDINYL)PIPERAZINYLALKYLAZASPIROALKANEDIONE PROCESS

FIELD OF THE INVENTION

This invention relates to novel spiro-quaternary ammonium halides and method of preparation. The instant invention is also concerned with use of the spiro-quaternary ammonium halide compounds in synthesis of U.S. Pat. No. 3,717,634 "N-(2-pyrimidyl)piperazinylalkylazospiroalkanediones" which are of value as psychopharmacologic agents.

DESCRIPTION OF THE PRIOR ART

Yao Hua Wu, et al., U.S. Pat. No. 3,717,634 disclose methods for synthesis of N-(heteroarcyclic)-piperazinylalkylazaspiroalkanediones including the following.

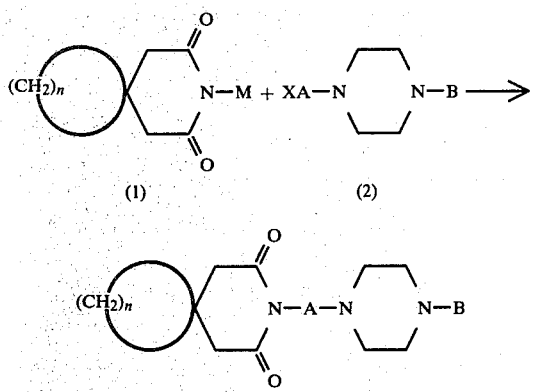

In the above reaction scheme, "n" is the integer 4 or 5, "M" comprises an alkali metal salt such as sodium or potassium; "X" inter alia is chlorine, bromine, iodine; and the symbol "A" connecting the spiroglutarimide and the N-(heteroarcyclic)piperazine represents a divalent alkylene chain of 2 to 6 carbon atoms inclusive. The symbol "B" represents inter alia various heterocyclic radicals including "2-pyrimidinyl".

The instant process differs from the Wu, et al., U.S. Pat. No. 3,717,634 patent process above in that alkylation of the spiroglutarimide is carried out directly with novel spiro-quaternary ammonium halides in the presence of base without prior formation of the spiroglutarimide metal salt (1).

SUMMARY OF THE INVENTION

Broadly described, this invention is concerned with new and useful spiro-quaternary ammonium halides generally typified by Formula I

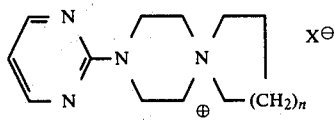 (I)

and use thereof in synthesis of N-(2-pyrimidinyl)-piperazinylalkylazaspiroalkanediones having psychopharmacologic properties.

DETAILED DESCRIPTION OF THE INVENTION

As indicated hereinabove, one embodiment of the instant invention relates to spiro-quaternary ammonium halide compounds of Formula I

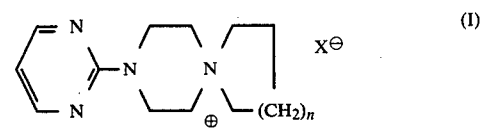 (I)

wherein n is equal to 1 or 2 and X is chlorine, bromine, or iodine obtained by a process which comprises treating 1-(2-pyrimidinyl)piperazine of Formula II

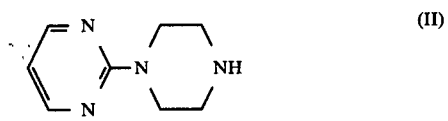 (II)

with a dihaloalkane of Formula III $$X-CH_2CH_2(CH_2)_nCH_2-X'$$ (III)

wherein n is equal to 1 or 2 and X and X' are independently selected from the group consisting of chlorine, bromine, and iodine.

In carrying out the process, the reactants are combined in a reaction inert liquid medium in the presence of a strong base such as an alkali metal oxide, hydroxide, amide, alcoholate or carbonate with sodium carbonate and potassium carbonate particularly preferred. Liquid reaction media boiling in the range of about 80° to 160° C. are preferred with the reaction conveniently carried out at the boiling point of the medium selected. Suitable reaction inert media include dimethylformamide as well as such liquid hydrocarbons, hydrocarbon nitriles, hydrocarbon ethers, and alkanols as xylene, acetonitrile, dibutylether, isopropanol, n-butanol and the like. Suitable reaction periods range from 2 to 24 hours with the duration of the reaction period depending to some extent upon the temperature and reaction solvent selected. In general, higher temperatures facilitate formation of the quaternary ammonium halides of Formula I.

Another embodiment of the instant invention is concerned with a process for preparing N-(2-pyrimidinyl)-piperazinylalkylazaspiroalkanediones of Formula IV

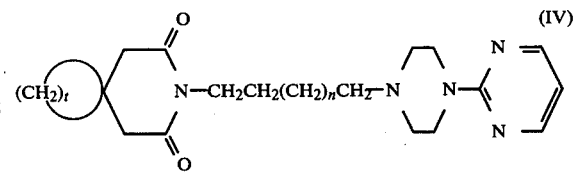 (IV)

wherein n is equal to 1 or 2 and t is equal to 4 or 5 which comprises condensing a spiro-quaternary ammonium halide compound of Formula I

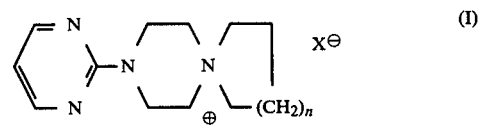 (I)

wherein n is equal to 1 or 2 and X is chlorine, bromine, or iodine with a spiro-substituent glutarimide of Formula V

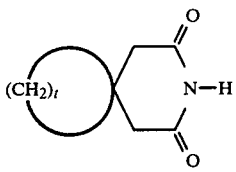

(V)

wherein t is 4 or 5 in substantially equimolar proportions in a liquid reaction medium in the presence of a strong base such as sodium carbonate, potassium carbonate and the like. In carrying out said process, reaction conditions employed in the process for preparing spiro-quaternary ammonium halide compounds of Formula I described herein are operable. Thus, condensation of a spiro-quaternary ammonium halide compound of Formula I with a glutarimide of Formula V is carried out in the reaction inert liquid medium in the presence of a strong base such as an alkali metal oxide, hydroxide, amide, alkali or carbonate with sodium carbonate and potassium carbonate particularly preferred. Liquid reaction media boiling in the range of about 80° C. are preferred with the reaction conveniently carried out at the boiling point of the medium selected. Suitable reaction inert media include dimethylformamide as well as such liquid hydrocarbons, hydrocarbon nitriles, hydrocarbon ethers, and alkanols as xylene, acetonitrile, dibutylether, isopropanol, n-butanol and the like. Suitable reaction periods range from 2 to 24 hours with the duration of the reaction period depending to some extent upon the temperature and reaction solvent selected.

A preferred embodiment of the present invention is a process for the preparation of 8-[4-[4(2-pyrimidinyl)-1-piperazinyl]butyl]-8-azaspiro[4,5]decane-7,9-dione of Formula IVa

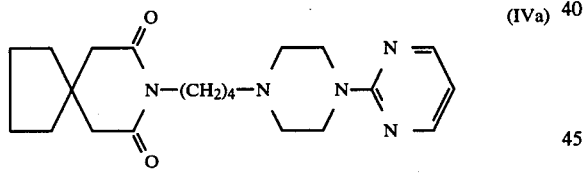

(IVa)

which comprises condensing a spiro-glutarimide of Formula Va

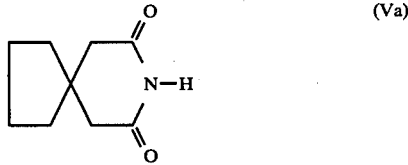

(Va)

with a spiro-quaternary ammonium halide of Formula Ia

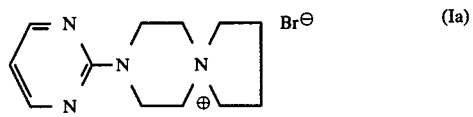

(Ia)

in a liquid reaction medium in the presence of a strong base. Further preferred embodiments of the foregoing process for preparation of 8-[4-[4-(2-pyrimidinyl)-1-piperazinyl]butyl]-8-azaspiro[4.5]decane-7,9-dione are those wherein the reaction is carried out in dimethylformamide in the presence of potassium carbonate.

The following non-limiting examples illustrate the present invention and will enable others skilled in the art to understand it more completely.

EXAMPLE 1

8-(2-Pyrimidinyl)-8-aza-5-azoniaspiro[4.5]decane Chloride

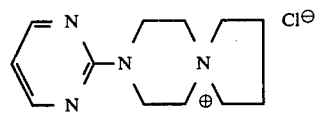

A mixture of 1-(2-pyrimidinyl)piperazine (32.8 g., 0.2 mole), 1,4-dichlorobutane (76.2 g., 0.6 mole) and finely powdered sodium carbonate (44.5 g., 0.42 mole) in 300 ml. of acetonitrile is stirred and refluxed for a 12-hour period. The hot reaction mixture is filtered and the filter cake washed with 50–100 ml. of hot acetonitrile. Combined filtrates are maintained at room temperature until crystallization occurs, then cooled, filtered, and collected material washed with acetone to provide a 70–90% yield of 8-(2-pyrimidinyl)-8-aza-5-azoniaspiro[4.5]decane chloride. This material is hygroscopic and after drying under vacuum at room temperature affords the monohydrate from melting about 90° C. which on continued drying under vacuum at 90° C. for several hours affords the anhydrous product having a melting point of about 210° C.

EXAMPLE 2

8-(2-Pyrimidinyl)-8-aza-5-azoniaspiro[4.5]decane Bromide

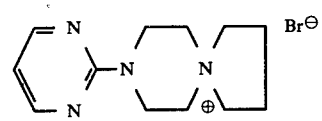

Reaction of 1-(2-Pyrimidinyl)piperazine and 1,4-Dibromobutane

A mixture of 1-(2-pyrimidinyl)piperazine (32.8 g., 0.2 mole), 1,4-dibromobutane (108 g., 0.5 mole) and finely powdered sodium carbonate (21.2 g., 0.2 mole) in 400 ml. of isopropanol is stirred and refluxed for a 16 hour period. The hot reaction mixture is filtered and the filtrate on standing at room temperature provides 50.3 g. (84% yield) of product. Crystallization of this material from isopropanol affords analytically pure 8-(2-pyrimidinyl)-8 -aza-5-azoniaspiro[4.5]decane bromide, m.p. 241.5°–242.5° C. (corr.).

Anal. Cacld. for $C_{12}H_{19}N_4.Br$ (percent): C, 48.17; H, 6.40; N, 18.72; Br, 26.71. Found (percent): C, 48.39; H, 6.53; N, 18.64; Br, 26.60.

Reaction of 1-(2-Pyrimidinyl)piperazine and 1,4-Dichlorobutane

A mixture of 1-(2-pyrimidinyl)piperazine (16.4 g., 0.1 mole), 1,4-dichlorobutane (23.8 g., 0.19 mole), sodium carbonate monohydrate (30.8 g., 0.25 mole) and potassium bromide (44.6 g., 0.375 mole) in 150 ml. of isopropanol is stirred and refluxed for an 8-hr. period. The hot reaction mixture is filtered and insolubles washed with hot isopropanol. Concentration of the combined filtrates under reduced pressure and trituration of residual material with acetone provides 8-(2-pyrimidinyl)-8-aza-5-azoniaspiro[4.5]decane bromide in yields of 50-90%.

EXAMPLE 3

3-(2-Pyrimidinyl)-3-aza-6-azoniaspiro[5.5]undecane Chloride

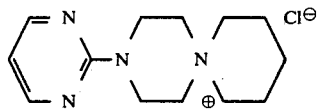

Reaction of 1-(2-pyrimidinyl)piperazine (16.4 g., 0.1 mole), 1,5-dichloropentane (28.2 g., 0.2 mole) and sodium carbonate (21.2 g., 0.2 mole) in 300 ml. of isopropanol according to the procedure of Example 2 affords the title compound.

EXAMPLE 4

3-(2-Pyrimidinyl)-3-aza-6-azoniaspiro[5.5]undecane Bromide

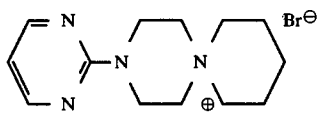

A mixture of 1-(2-pyrimidinyl)piperazine (24.6 g., 0.15 mole), 1.5-dibromopentane (100 g., 0.43 mole) and powdered sodium carbonate (31.8 g., 0.3 mole) in 400 ml. of isopropanol is refluxed for an 18 hour period and then filtered. On standing, the cooled filtrate provides 44.1 g. (94% yield) of product, m.p. 225-230° C. Crystallization from ispropanol affords analytically pure 3-(2-pyrimidinyl)-3-aza-6-azoniaspiro[5.5]undecane bromide, m.p. 232°-233° C.

Anal. Calcd. for $C_{13}H_{21}N_4.Br$ (percent): C, 49.85; H, 6.76; N, 17.89; Br, 25.51. Found (percent): C, 50.03; H, 6.87; N, 17.84; Br, 25.44.

EXAMPLE 5

8-[4-[4-(2-Pyrimidinyl)-1-piperazinyl]-butyl]-8-azaspiro[4.5]decane-7,9-dione

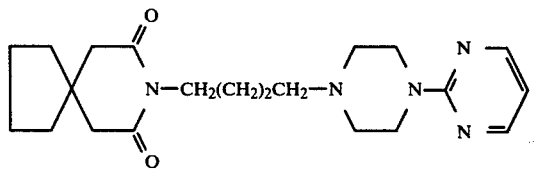

Reaction in n-Butanol

A mixture of 3,3-tetramethyleneglutarimide (7.5 g., 0.045 mole), 8-(2 -pyrimidinyl)-8-aza-5-azoniaspiro[4.5]-decane bromide (15.4 g., 0.045 mole), potassium carbonate (6.2 g., 0.045 mole) in 250 ml. of n-butanol is refluxed for a 21 hour period, filtered and evaporated to dryness. Residual material is warmed 45 minutes with acetic anhydride and evaporated to dryness. Water is added to the residue and the mixture basified with aqueous sodium hydroxide. Insolubles are collected and washed with water to provide 11.5 g. (66.5% yield) of 8-[4-[4-(2-pyrimidinyl)-1-piperazinyl]butyl]-8l-azaspiro[4.5]decane-7,9-dione as the free base, m.p. 90°-98° C.

The free base taken up in isopropanol and treated with concentrated hydrochloric acid provides the hydrochloride salt. Crystallization from isopropanol affords analytically pure 8-[4-[4-(2-pyrimidinyl)-1-piperazinyl]butyl]-8-azaspiro[4.5]decane-7,9-dione hydrochloride.

Anal. Calcd. for $C_{21}H_{31}N_5O_2.HCl$ (percent): C, 59.77; H, 7.65; N, 16.60; Cl, 8.40. Found (percent): C, 60.07; H, 7.72; N, 16.74; Cl, 8.27.

Reaction in dimethylformamide

A mixture 3,3-tetramethyleneglutarimide (16.7 g., 0.1 mole) , 8-(2-pyrimidinyl)-8-aza-5-azoniaspiro[4.5]decane bromide (29.9 g., 0.1 mole) and potassium carbonate (16.6 g., 0.12 mole) in 190 ml. of dimethylformamide is maintained at 150°-155° C. for a reaction period of 24 hours and then evaporated to dryness under reduced pressure. The resulting solid is triturated with 90 ml. of water, taken up in 10% hydrochloric acid and filtered. The acid filtrate is made basic with 10% aqueous sodium hydroxide and precipitated free base collected and dried to provide 8-[4-[4-(2-pyrimidinyl)-1-piperazinyl]-butyl]-8-azaspiro[4.5]decane-7,9-dione.

Following the above procedure but employing 8-(2-pyrimidinyl)-8-aza-5-azsoniaspiro[4.5]decane chloride monohydrate (27.3 g., 0.1 mole) in place of the corresponding quaternary bromide affords the title compound as the free base in about 80% yield, m.p. 100° C.

What is claimed is:

1. A process for the preparation of an N-(2-pyrimidinyl)-piperazinylalkylazaspiroalkanedione of Formula IV

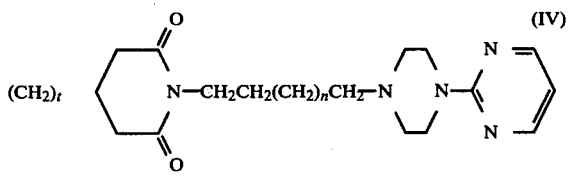

wherein n is equal to 1 or 2 and t is equal to 4 or 5 which comprises condensing a spiro-quaternary ammonium halide compound of formula I

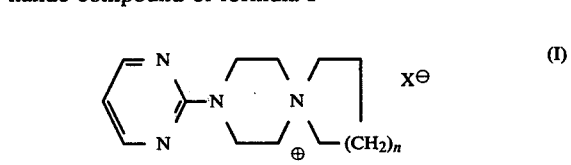

wherein n is equal to 1 or 2 and X is chlorine, bromine, or iodine with a spiro-substituted glutarimide of Formula V

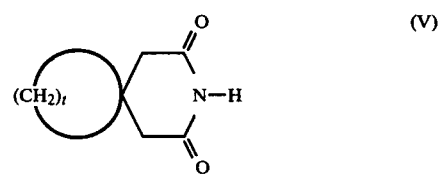

wherein t is 4 or 5 in a liquid reaction medium in the presence of a strong base.

2. The process of claim 1 wherein the compound of Formula I is 8-(2-pyrimidinyl)-8-aza-5-azoniaspiro[4.5]-decane chloride.

3. The process of claim 1 wherein the compound of Formula I is 8-(2-pyrimidinyl)-8-aza-5-azoniaspiro[4.5]-decane bromide.

4. A process for the preparation of 8-[4-[4-(2-pyrimidinyl)-1-piperazinyl]butyl]-8 azaspiro[4.5]decane-7,9-dione of Formula IVa

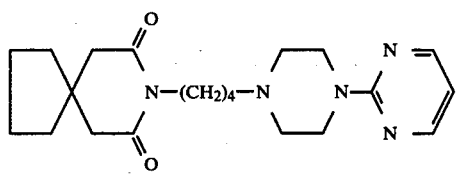

which comprises condensing a spiro-glutarimide of Formula Va

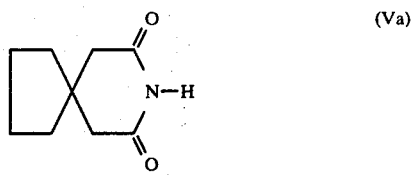

with a spiro-quaternary ammonium halide of Formula Ia

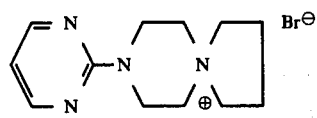

in a liquid reaction medium in the presence of a strong base.

* * * * *